United States Patent
Pruns et al.

(10) Patent No.: US 11,752,078 B2
(45) Date of Patent: Sep. 12, 2023

(54) OIL-IN-WATER EMULSIONS CONTAINING 4-HYDROXYACETOPHENONE AND ANIONIC EMULSIFIERS

(71) Applicant: Symrise AG, Holzminden (DE)

(72) Inventors: Julia Pruns, Hamburg (DE); Thomas Raschke, Pinneberg (DE); Bente Nissen, Hamburg (DE)

(73) Assignee: Symrise AG, Holzminden (DE)

( * ) Notice: Subject to any disclaimer, the term of this patent is extended or adjusted under 35 U.S.C. 154(b) by 985 days.

(21) Appl. No.: 15/128,300

(22) PCT Filed: Jan. 27, 2015

(86) PCT No.: PCT/EP2015/051554
§ 371 (c)(1),
(2) Date: May 10, 2018

(87) PCT Pub. No.: WO2015/144333
PCT Pub. Date: Oct. 1, 2015

(65) Prior Publication Data
US 2018/0243189 A1 Aug. 30, 2018

(30) Foreign Application Priority Data
Mar. 26, 2014 (DE) .................... 10 2014 104 255.7

(51) Int. Cl.
| | |
|---|---|
| *A61K 8/35* | (2006.01) |
| *A61K 8/36* | (2006.01) |
| *A61Q 19/00* | (2006.01) |
| *A61K 8/44* | (2006.01) |
| *A61K 8/55* | (2006.01) |
| *A61K 8/06* | (2006.01) |
| *A61Q 17/04* | (2006.01) |
| *A61K 8/46* | (2006.01) |

(52) U.S. Cl.
CPC ............... *A61K 8/35* (2013.01); *A61K 8/062* (2013.01); *A61K 8/361* (2013.01); *A61K 8/44* (2013.01); *A61K 8/442* (2013.01); *A61K 8/463* (2013.01); *A61K 8/55* (2013.01); *A61Q 17/04* (2013.01); *A61Q 19/00* (2013.01); *A61Q 19/005* (2013.01); *A61K 2800/43* (2013.01)

(58) Field of Classification Search
CPC ........................................................ A61K 8/35
See application file for complete search history.

(56) References Cited

U.S. PATENT DOCUMENTS

| | | | | |
|---|---|---|---|---|
| 5,085,857 | A * | 2/1992 | Reid | A61K 8/06 424/496 |
| 7,601,340 | B2 * | 10/2009 | Nojiri | A61K 8/046 424/70.11 |
| 9,040,026 | B2 * | 5/2015 | Doyle | A61K 8/86 424/60 |
| 2007/0161524 | A1 * | 7/2007 | Counradi | A61K 8/44 510/130 |
| 2007/0269390 | A1 | 11/2007 | Inoue | |
| 2013/0059924 | A1 * | 3/2013 | Scheurich | A61K 8/40 514/772 |
| 2014/0017184 | A1 * | 1/2014 | Fumagalli | C11D 3/3757 424/59 |
| 2016/0000670 | A1 * | 1/2016 | Pesaro | A61Q 5/02 424/59 |

FOREIGN PATENT DOCUMENTS

| | | |
|---|---|---|
| DE | 10 2010 063888 A1 | 6/2012 |
| EP | 2 774 481 A1 | 9/2014 |
| EP | 2 774 604 A1 | 9/2014 |
| JP | 07206645 A * | 8/1995 |
| JP | H07206645 * | 8/1995 |
| KR | 20130134976 A * | 12/2013 |

OTHER PUBLICATIONS

Symrise Internet Citation, "Multiple Benefits for Cosmetics with SymSave H," Jul. 26, 2013.
Rajabi et al, "Acetophenones with selective antimycobacterial activity," Letters in Applied Microbiology vol. 40, No. 3, Mar. 1, 2005, pp. 212-217.

* cited by examiner

*Primary Examiner* — Gina C Justice
(74) *Attorney, Agent, or Firm* — Dilworth & Barrese, LLP

(57) ABSTRACT

The invention relates to oil-in-water emulsions containing 4-hydroxyacetophenone and anionic emulsifiers.

3 Claims, No Drawings

OIL-IN-WATER EMULSIONS CONTAINING 4-HYDROXYACETOPHENONE AND ANIONIC EMULSIFIERS

BACKGROUND OF THE INVENTION

The present invention relates to cosmetic or dermatological preparations containing active agents for the protection of sensitive skin against irritations and the use of these active agents and combinations of these active agents in the field of cosmetic and dermatologic skin care. In an advantageous embodiment, the present invention relates to a use that permits to increase the stability of emulsions, gels, aqueous preparations or fat formulations.

The outer layer of the epidermis, the stratum corneum (horny layer), is of a particular significance as an important barrier layer, among others, for the protection against environmental influences and against drying. The horny layer corneum is constantly eroded while in contact with the environment and thus needs to be continuously regenerated.

A skin model widely known in expert circles today considers the stratum corneum a two-component-system, similar to a brick wall (brick-and-mortar-model). According to this model, the corneocytes (horny cells) correspond to the bricks, and the lipid membrane in the intercellular spaces, which is of complex composition, corresponds to the mortar.

Apart from their barrier action against external chemical and physical influences, the epidermal lipids also contribute to the holding together of the horny layer and have an effect on the smoothness of the skin. In contrast to the sebaceous gland lipids, which do not form a continuous film on the skin, the epidermal lipids are distributed over the entire horny layer.

The extremely complex interaction of the moisture-binding substances and of the lipids of the upper layers of the skin is very important for the regulation of skin moisture. For this reason, cosmetics generally comprise, in addition to balanced lipid mixtures and water, water-binding substances.

As well as the chemical composition, however, the physical behaviour of these substances is also of importance. The development of very biocompatible emulsifiers and surfactants with liquid-crystalline properties is therefore desirable. Products formulated therewith aid the liquid-crystalline organization of the intercellular lipids of the stratum corneum, thereby improving the barrier properties of the horny layer. It is particularly advantageous if their molecular constituents consist of substances which are naturally occurring in the epidermis.

Cosmetic skin care primarily means that the natural function of the skin as a barrier against environmental influences (e.g. dirt, chemicals, microorganisms) and against the loss of endogenous substances (e.g. water, natural fats, electrolytes) is strengthened or restored.

If this function is impaired, increased resorption of toxic or allergenic substances or attack by microorganisms may result, leading to toxic or allergic skin reactions.

Another aim of skin care is to compensate for the loss by the skin of lipids and water caused by daily washing. This is particularly important when the natural regeneration ability is insufficient. Furthermore, skin care products should protect against environmental influences, in particular against sun and wind, and delay skin aging.

Medicinal topical compositions generally comprise one or more medicaments in an effective concentration. For the sake of simplicity, in order to distinguish clearly between cosmetic and medicinal use and corresponding products, reference is made to the legal provisions in the Federal Republic of Germany (e.g. Cosmetics Directive, Foods and Drugs Act).

Regular cosmetic dosage forms are emulsions, i.e. metastable two-phase or multiple phase systems in which the individual phases are present in a liquid state. The most common emulsions are O/W and W/O emulsions. Less common forms of application are multiple emulsions, i.e. those which, in the droplets of the dispersed (or discontinuous) phase, comprise for their part droplets of a further dispersed phase, e.g. W/O/W emulsions and O/W/O emulsions.

In order to be able to ensure the metastability of emulsions, interface-active substances, i.e. emulsifiers, are usually necessary.

The use per se of customary cosmetic emulsifiers is entirely acceptable. Nevertheless, emulsifiers, as ultimately any chemical substance, may in certain cases cause allergic reactions or reactions based on oversensitivity of the user. For example, it is known that in some particularly sensitive people, certain light dermatoses are triggered by certain emulsifiers and simultaneous action of sunlight.

It is possible to prepare emulsifier-free preparations which, for example, have, in an aqueous phase, dispersed oil droplets, similar to an O/W emulsion. A prerequisite for this may be that the continuous aqueous phase has a gel framework which stabilizes the dispersed phase, and other conditions besides. Such systems are sometimes called hydrodispersions or oleodispersions depending on which is the disperse phase and which is the continuous phase.

For cosmetics technology, it is neither necessary nor possible to dispense with emulsifiers altogether, especially since there is a certain choice of particularly mild emulsifiers. However, the prior art lacks a satisfactorily broad range of such emulsifiers which would then also significantly broaden the application spectrum of correspondingly mild cosmetic preparations which are tolerated by the skin.

It was therefore an object of the present invention to provide cosmetic or dermatological preparations with outstanding skin-care properties.

A disadvantage, in particular of O/W emulsions, often is their lack of stability compared with higher electrolyte concentrations, which manifests itself in a phase separation. This, however, may occasionally lead to problems in W/O emulsions as well, but is by far not as prominent as in the case of O/W systems. It is possible to remedy this to a certain extent by selecting a suitable emulsifier system, but other disadvantages are then encountered quite as often.

On the other hand it is often desirable to employ particular electrolytes in order to use their other physical, chemical or other properties.

Further, increased heavy metal concentrations caused by production performed in containers, stirrers, pipelines, etc., which are made of steel considerably decreases the stability of cosmetic preparations. A complexation of unwelcome metals such as Mn, Fe, Cu and others, for example, may prevent undesired chemical reactions in cosmetic or dermatological preparations.

Complexing agents, particularly, chelators, form complexes with metal atoms which in the presence of one or more multiple-base complexing agents, i.e., chelators, represent metal cycles. Chelates represent compounds in which an individual ligand occupies more than one coordination sites at a central atom. In this case, the normally stretched compounds are closed to form rings during the formation of complexes by means of a metal atom or a metal ion. The number of bonded ligands depends on the coordination number of the central metal. A prerequisite for the formation of chelates is that the compound that reacts with the metal contains two or more atom groupings that are acting as electron donors.

There is a disadvantage in many chelators in that they are not easily biodegradable and are almost inevitably introduced into the ecological water cycle. A solubilization of heavy metal ions that are present in precipitated form or bound in sediments—being, therefore, relatively harmless—may, in the worst case, contribute to their reactivation.

It was thus a further object of the present invention to discover solutions for cosmetic or dermatological emulsions, particularly O/W emulsions, which are stable against increased electrolyte concentrations, or increased ionic strengths, or heavy metal ions.

Customary, and just recently increasingly widespread cosmetic and dermatological preparation forms are gels. In the technical sense gels are understood as meaning: relatively dimensionally stable, easily deformable disperse systems of at least two components which as a rule consist of one—usually solid—colloidally dispersed substance formed of long-chain molecular groups (e.g. gelatin, silicic acid, polysaccharides) as structure-forming agents and a liquid dispersing agent (e.g. water). The colloidally dispersed substance is often described as a thickening or gelling agent. It forms a spatial network in the dispersing agent, it being possible for individual particles present in colloidal form to be more or less firmly linked to one another by means of electrostatic interaction. The dispersing agent, which surrounds the network, is distinguished by electrostatic affinity for the gelling agent, i.e. a predominantly polar (in particular: hydrophilic) gelling agent preferably gels a polar dispersing agent (in particular: water), whereas a predominantly non-polar gelling agent preferably gels non-polar dispersing agents.

Strong electrostatic interactions which are realized, for example, in hydrogening agent bonds between gelling agent and dispersant, but also mutually between dispersing agent molecules, can lead to strong cross-linking even of the dispersing agent. Hydrogels can consist almost to 100% of water (besides, for example, about 0.2-1.0% of a gelling agent) and at the same time have absolutely solid consistency. The water content is in this case present in ice-like structural elements, so that gels are therefore absolutely justified in the derivation of their name from the latin "gelatum"="congelation" via the alchemistic expression "gelatina" (16th Century) for current German "Gelatine".

In cosmetic and pharmaceutical technology, lipogels and oleogels (on the basis of waxes, fats and fatty oils) and also carbogels (on the basis of paraffin or petrolatum) are also known. In practice, a differentiation is made between oleogels, which are virtually water-free, and hydrogels, which are virtually fat-free. Usually, gels are transparent. In cosmetic or pharmaceutical technology, gels are generally distinguished by semi-solid, often fluid consistency.

Further, so-called surfactant gels are common preparations of the state of the art. These are understood as systems having a high concentration of emulsifiers in addition to water, typically more than ca. 25% by weight, based on the total composition. If oil components are solubilized into these surfactant gels which are technically also referred to as "surfactant gels", microemulsion gels are obtained, which are also referred to as "ringing gels". By adding non-ionic emulsifiers, for example, alkyl polyglycosides, cosmetically more sophisticated microemulsion gels may be obtained.

Numerous cosmetic and dermatological active agents are known, including water-soluble ones —which, consequently, are predominantly present in the water phase of an emulsion—and oil-soluble ones—which, consequently, are predominantly present in the oil phase of an emulsion.

The log P value indicates the logarithmic coefficient of the partition coefficient octanol/water $K_{ow}$ and is a measure for the ratio between the lipophily (solubility in fats) and hydrophily (solubility in water) of a substance. It serves as a model estimation to see in which phase (oil or water) the substance is preferably solubilized or concentrated.

Accordingly, the log P is positive for lipophilic substances and negative for hydrophilic substances.

Thus, a log P value of three would mean that the active agent would distribute itself in an octanol/water mixture in the ratio of 1000:1. This means that it would be more highly concentrated in the oil phase by factor 1000. The same applies to substances having only a very low solubility in water. Also these substances are predominantly found in the lipid phase when formulated crystal-free.

Active agents which are predominantly present in the oil phase, are in the scope of this disclosure understood to mean substances having
a) a log P value≥2, or
b) a solubility of water≤2.5 g/L.

In the case of plant extracts this means that 0.25% solutions cannot be clearly solubilized.

Cosmetic and pharmaceutical active agents are often, but far from always, stable against environmental influences. Numerous instabilities are known against oxygen—or, generally, against redox processes—and against UV light, but also against heat and other factors.

Cosmetic ingredients which are known to be sensitive against such processes include natural plant oils with a portion of unsaturated fatty acids (e.g., sunflower oil and evening primrose oil), vitamin A and its derivatives, vitamin C and its derivatives, plant extracts with a portion of polyphenols such as, for example, green tea and liquorice, organic colouring agents and synthetic polymers from the group consisting of polyacrylates.

SUMMARY OF THE INVENTION

A known and highly effective antioxidant is 4-hydroxyacetophenone, which is, among others, marketed by the company Symrise under the trade name "SymSave® H". It has the CAS No. 99-93-4 and is characterized by the following chemical structure
(Formel)

Surprisingly it has shown, and in this the solution of these objects is based, that the use of 4-hydroxyacetophenone for obtaining or increasing the stability of cosmetic preparations which are present in the form of O/W emulsions, remedy the disadvantages of the state of the art.

The term "obtaining or increasing the stability" means that a corresponding formulation, which is characterized in that it contains 4-hydroxyacetophenone shows a higher stability than a corresponding formulation without 4-hydroxyacetophenone.

In doing so, a formulation characterized in that it contains 4-hydroxyacetophenone is compared with one in which the proportion by weight of 4-hydroxyacetophenone was replaced by a corresponding proportion by weight of water or of the main oil component of the preparation.

In this context, the term "stability" is intended to mean that the product with 4-hydroxyacetophenone is protected against phase separation for a longer time and/or at higher temperatures than a product without 4-hydroxyacetophenone.

The term "stability" may also mean that if the product with 4-hydroxyacetophenone contains a colouring agent, the colouring agent is protected against chemical decomposition for a longer time and/or at higher temperatures and/or at a higher dose of light than a product without 4-hydroxyacetophenone.

The term "stability" may also mean that if the product with 4-hydroxyacetophenone contains a perfume component or a cosmetic fragrance component this agent is protected against chemical decomposition for a longer time and/or at higher temperatures and/or at a higher dose of light than a product without 4-hydroxyacetophenone.

The term "stability" may also mean that if the product with 4-hydroxyacetophenone contains a cosmetic or dermatological active agent this active agent is protected against chemical decomposition for a longer time and/or at higher temperatures and/or at a higher dose of light than a product without 4-hydroxyacetophenone.

The skilled person could not foresee that the preparations of the invention could have a higher stability and be characterized by an increased biocompatibility than the preparations of the state of the art.

Preparations according to the invention are advantageously characterized in that they have a content of 0.01 to 10% by weight, particularly, 0.05 to 3.0% by weight, of 4-hydroxyacetophenone, particularly, 4-hydroxyacetophenone, each based on the total weight of the preparation.

DETAILED DESCRIPTION OF THE INVENTION

It is particularly advantageous within the meaning of the present invention to keep the content of customary complexing agents low, or to dispense with using them altogether, such as those selected from the group consisting of ethylenediaminetetraacetic acid (EDTA) and its anions, nitrilotriacetic acid (NTA) and its anions, hydroxyethylenediaminetriacetic acid (HOEDTA) and its anions, diethyleneaminepentaacetic acid (DPTA) and its anions, trans-1,2-diaminocyclohexanetetraacetic acid (CDTA) and its anions. In any case, a content of ca. 0.5% by weight of these complex formers, based on the total weight of the preparations, should preferably not be exceeded.

The manufacture of preparations according to the invention is performed according to the common rules known to the skilled person.

It is possible and advantageous to add 4-hydroxyacetophenone at the beginning of the process of manufacture of the water phase or the oil phase. However, the solubility of 4-hydroxyacetophenone in the water phase and, particularly, in the oil phase is limited.

The cosmetic preparations according to the invention may contain cosmetic adjuvants, such as are normally used for such preparations, e.g., preservatives, bactericides, deodorants, anti-perspirants, insect repellents, vitamins, anti-foaming agents, colouring agents, pigments having a colouring effect, thickeners, softeners, wetting and/or moisturizing substances, fats, oils, waxes or other common components of a cosmetic formulation such as alcohols, polyols, polymers, foam stabilizers, electrolytes, organic solvents or silicone derivatives.

Advantageously, the preparations according to the invention may additionally contain substances, which absorb UV radiation in the UVB range, whereby the total amount of filter substances is, e.g., 0.1% by weight to 30% by weight, preferably 0.5 to 10% by weight, particularly 1.0 to 6.0% by weight, based on the total weight of the preparation, to provide cosmetic preparations protecting the hair and the skin against the whole range of ultraviolet radiation. They may also be used as a sun-screen agent for the hair.

In case the preparations according to the invention contain UVB filter substances, these may be oil soluble or water soluble. According to the invention, advantageous oil soluble UVB filters are, e.g.:
  3-benzylidenecamphor and its derivatives, e.g. 3-(4-methylbenzylidene) camphor; 3-benzylidene camphor
  4-aminobenzoic acid derivatives, preferably, 2-ethylhexyl 4-dimethylaminobenzoate, amyl 4-dimethylaminobenzoate,
  esters of cinnamic acid, preferably 2-ethylhexyl 4-methoxycinnamate, isopentyl 4-methoxycinnamate;
  esters of salicylic acid, preferably 2-ethylhexyl salicylate, 4-isopropylbenzyl salicylate, homomenthyl salicylate;
  derivatives of benzophenone, preferably 2-hydroxy-4-methoxybenzophenone, 2-hydroxy-4-methoxy-4'-methylbenzophenone, 2,2'-dihydroxy-4-methoxybenzophenone;
  esters of benzylidenemalonic acid, preferably di(2-ethylhexyl) 4-methoxybenzylidenemalonates;
  2,4,6-trianilino(p-carbo-2'-ethyl-1'-hexyloxy)-1,3,5-triazine.

Advantageous water-soluble UVB filters are, e.g.,:
  salts of the 2-phenylbenzimidazole-5-sulfonic acid such as its sodium, potassium or triethanolammonium salt, and the sulfonic acid itself;
  sulfonic acid derivatives of benzophenones, preferably, 2-hydroxy-4-methoxybenzophenone-5-sulfonic acid and its salts;
  sulfonic acid derivatives of 3-benzylidencamphor, such as, e.g., 4-(2-oxo-3-bornylidenmethyl)benzenesulfonic acid, 2-methyl-5-(2-oxo-3-bornylidenmethyl) sulfonic acid and its salts and 1,4-di(2-oxo-10-sulfo-3-bornylidenmethyl)-benzene and its salts (the corresponding 10-sulfate compounds, for example, the corresponding sodium, potassium or triethanolammonium salt), also referred to as benzene-1,4-di(2-oxo-3-bornylidenmethyl-10-sulfonic acid.

The list of UVB filters to be used according to the invention stated is certainly not intended to be limiting.

It may also be advantageous to employ in preparations according to the invention UVA filters which are customarily contained in cosmetic preparations. Such filter substances are preferably derivatives of dibenzoylmethane, in particular 1-(4'-tert-butylphenol)-3-(4'-methoxphenyl)propane-1,3-dione and 1-phenyl-3-(4'-isopropylphenyl)propane-1,3-dione. The same amounts of UVA filter substances can be used which were mentioned for UVB filter substances.

According to the invention, cosmetic and dermatological preparations further advantageously comprise inorganic pigments on the basis of metal oxides and/or other metal compounds that are slowly soluble or insoluble in water, particularly the oxides of titanium ($TiO_2$), zinc (ZnO), iron (e.g., $Fe_2O_3$), zirconium ($ZrO_2$), silicium ($SiO_2$), manganese (e.g., MnO), aluminium ($Al_2O_3$), cerium (e.g., $Ce_2O_3$), mixed oxides of the corresponding metals and mixtures of such oxides. Particular preference is given to pigments based on titanium dioxide.

It is particularly advantageous within the meaning of the present invention, although not mandatory, if the inorganic pigments are present in hydrophobic form, i.e., that they have received hydrophobical treatment on their surfaces.

This surface treatment may consist in applying a thin hydrophobic coating onto the pigments according to known processes.

One of these processes, for example, consists in creating the hydrophobic surface coating by means of a reaction according to $$n\ TiO_2 + m\ (RO)_3Si-R' \to n\ TiO_2(surf.)$$

wherein n and m are stoichiometric parameters to be optionally employed, R and R' are the desired organic moieties. Hydrophobised pigments are advantageous which are represented, for example, in analogy to DE-OS 33 14 742.

Advantageous $TiO_2$ pigments are, for example, available under the trade names MT 100 T from the company TAYCA, further, as M 160 from the company Kemira and as T 805 from the company Degussa.

Preparations according to the invention may also contain anionic, non-ionic and/or amphoteric surfactants, particularly in the case when crystalline or micro-crystalline solids, such as, for example, inorganic micropigments, are to be introduced into the preparations according to the invention. Surfactants are amphiphilic substances which can solubilize organic, non-polar substances in water.

The hydrophilic portions of a surfactant molecule are mostly polar functional groups, for example, $-COO^-$, $-OSO_3^{2-}$, $-SO_3^-$, while the hydrophobic portions usually represent non-polar hydrocarbon moieties. Surfactants are generally classified according to the type and charge of the hydrophilic molecule portion. Four groups can be distinguished here:
- anionic surfactants,
- cationic surfactants,
- amphoteric surfactants, and
- non-ionic surfactants.

As functional groups, anionic surfactants usually contain carbon/late, sulfate or sulfonate groups. In aqueous solution they form negatively charged organic ions in an acid or neutral environment. Cationic surfactants are almost exclusively characterized by the presence of a quaternary ammonium group. In aqueous solution, they form positively charged organic ions in an acid or neutral environment. Amphoteric surfactants contain both anionic and cationic groups and, as a result, they behave like anionic or cationic surfactants in an aqueous solution, depending on the pH value. In a strongly acid environment they have a positive charge, and in an alkaline environment they have a negative charge. However, in the neutral pH range they are zwitterionic, as is to be illustrated by the following example:
$RNH_2^+CH_2CH_2COOH\ X^-$ (at pH=2) X−=optional anion, e.g., $Cl^-$
$RNH_2^+CH_2CH_2COO^-$ (at pH=7)
$RNHCH_2CH_2COO^-$ (at pH=12) $B^+$=optional cation, e.g., $Na^+$ Typical for non-ionic surfactants are polyether chains. Non-ionic surfactants do not form ions in an aqueous environment.

A. Anionic Surfactants

Examples of anionic surfactants which are to be used advantageously are acylamino acids (and their salts), such as
1. Acyl glutamates, for example, Sodium Acyl Glutamate, Di-TEA-Palmitoyl Aspartate and Sodium Caprylic/Capric Glutamate,
2. Acyl peptides, for example, Palmitoyl Hydrolysed Milk Protein, Sodium Cocoyl Hydrolysed Soy Protein and Sodium/Potassium Cocoyl Hydrolysed Collagen,
3. Sarcosinates, for example, Myristoyl Sarcosin, TEA-Lauroyl Sarcosinate, Sodium Lauroyl Sarcosinate and Sodium Cocoyl Sarcosinate,
4. Taurates, for example, Sodium Lauroyl Taurate and Sodium Methyl Cocoyl Taurate,
5. Acyl lactylates, Lauroyl Lactylate, Caproyl Lactylate,
6. Alaninates.

Carboxylic acids and derivatives such as
1. Carboxylic acids, for example, Lauric Acid, Aluminium Stearate, Magnesium Alkanolate and Zinc Undecylenate,
2. Ester carboxylic acids, for example, Calcium Stearoyl Lactylate, Laureth-6-Citrate and Sodium PEG-4-Lauramide Carboxylate,
3. Ether carboxylic acids, for example, Sodium Laureth-13-Carboxylate and Sodium PEG-6-Cocamide Carboxylate, Phosphoric acid esters and salts such as, for example, DEA-Oleth-10-Phosphate and Dilaureth-4 Phosphate, Sulfonic acids and salts such as
1. Acyl isethionates, e.g., Sodium/Ammonium Cocoyl Isethionate,
2. Alkyl aryl sulfonates,
3. Alkyl sulfonates, for example, Sodium Coco Monoglyceride Sulfate, Sodium C12-14 Olefin Sulfonate, Sodium Lauryl Sulfoacetate and Magnesium PEG-3 Cocamide Sulfate,
4. Sulfosuccinates, for example, Dioctyl Sodium Sulfosuccinate, Disodium Laureth Sulfosuccinate, Disodium Lauryl Sulfosuccinate and Disodium Undecylenamido-MEA-Sulfosuccinate.

and sulfuric acid esters such as
1. Alkyl ether sulfates, for example, Sodium, Ammonium, Magnesium, MIPA-, TIPA Laureth Sulfate, Sodium Myreth Sulfate and Sodium Ci2-13 Pareth Sulfate,
2. Alkyl sulfates, for example, Sodium, Ammonium and TEA Lauryl Sulfate.

B. Cationic Surfactants

Examples of cationic surfactants which are to be used advantageously are
1. Alkyl amines,
2. Alkyl imidazoles,
3. Ethoxylated amines,
4. Quaternary surfactants,
5. Esterquats.

Quaternary surfactants contain at least one nitrogen atom which is covalently bonded to 4 alkyl or aryl groups. Irrespective of the pH, this leads to a positive charge. Alkylbetaine, alkylamidopropylbetaine and alkylamidopropylhydroxysulfaine are advantageous. The cationic surfactants used according to the invention can also preferably be chosen from the group of quaternary ammonium compounds, in particular benzyltrialkylammonium chlorides or bromides, such as, for example, benzyldimethylstearylammonium chloride, and also alkyltrialkylammonium salts, for example, cetyltrimethylammonium chloride or bromide, alkyldimethylhydroxyethylammonium chlorides or bromides, dialkyldimethylammonium chlorides or bromides, alkylamidoethyltrimethylammonium ether sulfates, alkylpyridinium salts, for example lauryl- or cetylpyrimidinium chloride, imidazoline derivates and compounds having a cationic character such as amine oxides, for example alkyldimethylamine oxides or alkylaminoethyidimethylamine oxide. In particular, cetyltrimethylammonium salts can be used advantageously.

C. Amphoteric Surfactants

Examples of amphoteric surfactants which are to be used advantageously are
1. acyl/dialkylethylenediamine, for example sodium acylamphoacetate, disodium acylamphodipropionate, disodium alkylamphodiacetate, sodium acylamphohydroxypropylsulfonate, disodium acylamphodiacetate and sodium acylamphopropionate,
2. N-alkylamino acids, for example aminopropylalkylglutamide, alkylaminopropionic acid, sodium alkylimidodipropionate and lauroamphocarboxyglycinate.

D. Non-Ionic Surfactants

Examples of non-ionic surfactants which are to be used advantageously are
1. Alcohols,
2. Alkanol amides, such as coco amido MEA/DEA/MIPA,
3. Amine oxides, such as coco amido propyl amine oxide,
4. Esters obtained by esterification of carboxylic acids with ethylene oxide, glycerol, sorbitane or other alcohols
5. Ethers, for example, ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanoline, ethoxy-lated/propoxylated polysiloxanes, propoxylated POE ethers, and alkyl polyglycosides such as lauryl glucoside, decyl glycoside and coco glycoside,
6. Sucrose esters and ethers
7. Polyglycerol esters, diglycerol esters, monoglycerol esters
8. Methyl glucose esters, esters of hydroxyacids.

Further, the use of a combination of anionic and/or amphoteric surfactants with one or more non-ionic surfactants is advantageous.

The surface-active substance may be present in a concentration between 1 and 95% by weight in the preparations according to the invention, based on the total weight of the preparations.

Preparations according to the invention may also be present in the form of cosmetic deodorants and/or antiperspirants. Deodorants are required to meet the following criteria:
1) They are required to provide a reliable deodorant effect.
2) Any natural biological processes of the skin must not be impaired by deodorants.
3) Deodorants must be harmless in the event of overdosage or other unappropriate use.
4) They must not concentrate on the skin after repeated application.
5) They are required to be easily incorporated into customary cosmetic formulations.

Both liquid deodorants, for example, aerosol sprays, roll-ons and the like, and solid preparations, for example, deodorant sticks ("sticks"), powder, powder sprays, intimate cleansers, etc., are known and customary.

For example, by means of astringents—mainly aluminium salts such as aluminium hydroxychloride—the formation of perspiration can be suppressed (aluminium chlorohydrate).

By the use of antimicrobial substances in cosmetic deodorants the bacterial flora on the skin can be reduced. At the same time, in the ideal case only the odour-causing microorganisms in the skin should be effectively reduced. The flow of perspiration itself will not be influenced, ideally only the microbial decomposition of perspiration is temporarily stopped.

Also the combination of adstringents with antimicrobially effective substances in one and the same composition is customary.

Beside the liquid desodorants also solid preparations are known and customary, for example, deodorant sticks ("sticks"), powders, powder sprays, intimate cleansers, etc.

The lipid phase of the cosmetic or dermatological emulsions according to the invention may preferably be selected from the following group of substances:
mineral oils, mineral waxes
oils such as capric/caprylic triglycerides, further, natural oils such as, e.g., castor oil;
fats, waxes and other natural and synthetic fat bodies, preferably, esters of fatty acids with low C number alcohols, e.g., with isopropanol, propylene glycol or glycerol, or esters of fatty acids with low C number alkanoic acids or with fatty acids;
alkyl benzoates;
silicone oils such as dimethylpolysiloxane, diethylpolysiloxane, diphenylpolysiloxane and mixtures thereof.

The oil phase of the emulsions within the meaning of the present invention may advantageously be selected from the group of esters consisting of saturated and/or unsaturated, branched and/or non-branched alkane carboxylic acids, having a chain length from 3 to 30 C atoms and saturated and/or unsaturated, branched and/or non-branched alcohols, having a chain length from 3 to 30 C atoms, from the group consisting of esters of aromatic carboxylic acids and saturated and/or unsaturated, branched and/or non-branched alcohols, having a chain length from 3 to 30 C atoms. Such ester oils may then be advantageously selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethyl hexyl palmitate, 2-ethyl hexyl laurate, 2-hexyl decyl stearate, 2-octyl dodecyl palmitate, oleyl oleate, oleyl erucate, erucyl oleate, erucyl erucate and synthetic, semi-synthetic and natural mixtures of such esters, e.g., jojoba oil.

Further, the oil phase may be advantageously selected from the group consisting of branched and non-branched hydrocarbons and hydrocarbon waxes, silicone oils, dialkyl ethers, the group consisting of saturated or unsaturated, branched or non-branched alcohols, as well as the fatty acid triglycerides, namely triglycerides of saturated and/or unsaturated, branched and/or non-branched alkane carboxylic acids, having a chain length from 8 to 24, particularly, 12-18 C atoms. The fatty acid triglycerides may be advantageously selected, for example, from the group consisting of synthetic, semi-synthetic and natural oils, e.g., olive oil, sunflower oil, soybean oil, peanut oil, rapeseed oil, almond oil, palm oil, coconut oil, palm kernel oil and the like.

Also advantageously applicable within the meaning of the present invention are any mixtures of these oil and wax components. Optionally, it may be advantageous to employ waxes, for example, cetyl palmitate, as a sole lipid component of the oil phase.

Advantageously, the oil phase is selected from the group consisting of 2-ethylhexyl isostearate, octyldodecanol, isotridecyl isononanoate, isoeicosane, 2-ethylhexyl cocoate, $C_{12-15}$-alkyl benzoate, caprylic/capric triglyceride, dicaprylyl ether.

Particularly advantageous are mixtures of $C_{12-15}$-alkyl benzoate and 2-ethylhexyl isostearate, mixtures of $C_{12-15}$-alkyl benzoate and isotridecyl isononanoate, and mixtures of $C_{12-15}$-alkyl benzoate, 2-ethylhexyl isostearate and isotridecyl isononanoate.

Among the hydrocarbons, paraffin oil, cycloparaffin, squalane, squalene, hydrated polyisobutene or polydecene may be advantageously used within the meaning of the present invention.

Preferably, the oil phase may contain cyclic and/or linear silicones or completely consist of these oils, wherein it is however preferred to use an additional content of other oil phase components in addition to the silicone oil or the silicone oils. These silicones or silicone oils can be present as monomers, which are usually characterized by structural elements, as follows
(Formel)

Advantageously applicable linear silicones with a plurality of siloxy units according to the invention are generally characterized by structural elements as follows
(Formel)
wherein the silicium atoms with the same or different alkyl moieties and/or aryl moieties can be substituted, which are represented here in a generalizing manner by the moieties R1-R4 (meaning that the number of different moieties is not required to be limited to up to 4), m may assume values from 2-200,000.

Cyclic silicones that are advantageously applicable according to the invention are generally characterized by structural elements as follows
(Formel)
wherein the silicium atoms can be substituted with the same or different alkyl moieties and/or aryl moieties, which are here represented in a generalizing manner by the moieties R1-R4 (meaning that the number of different moieties is not required to be limited to up to 4), n may here assume values from 3/2 bis 20. Broken values for n take into account that odd numbers of siloxy end groups may be present in the cycle.

Advantageously, the silicone oil selected is cyclotrimethicone (e.g., decamethylcyclopentasiloxane). Also other silicone oils, for example, polydimethylsiloxane, poly(m-ethylphenylsiloxane), cetyl dimethicone, behenoxydimethicone may be advantageously used within the meaning of the present invention.

However, it is also advantageous to select silicone oils having a similar constitution as the above designated compounds, wherein the organic side branches are derivatised, for example, polyethoxylated and/or polypropoxylated. This includes, for example, polysiloxane polyalkyl polyether copolymers such as cetyl dimethicone copolyol, (cetyl dimethicone copolyol (and) polyglyceryl-4-isostearate (and) hexyl laurate).

Particularly advantageous are, further, mixtures of cyclomethicone and isotridecyl isononanoate, of cyclomethicone and 2-ethylhexyl isostearate.

The aqueous phase of the preparations according to the invention, optionally, advantageously comprises low C number alcohols, diols or polyols, as well as their ethers, preferably, ethanol, isopropanol, propylene glycol, glycerol, ethylene glycol, ethylene glycol monoethyl or monobutyl ether, propylene glycol monomethyl, -monoethyl- or -monobutyl ether, diethylene glycol monomethyl- or -monoethyl ether and analogous products, further low C number alcohols, e.g., ethanol, isopropanol, 1,2-propanediol, glycerol and, particularly, one or more thickeners which may advantageously selected from the group consisting of silicon dioxide, aluminium silicates.

Particularly advantageously, the preparations according to the invention that are present as emulsions contain one or more hydrocolloids. These hydrocolloids may be advantageously selected from the group consisting of gums, polysaccharides, cellulose derivatives, phyllosilicates, polyacrylates and/or other polymers.

According to the invention, the preparations that are present as hydrogels contain one or more hydrocolloids. These hydrocolloids may be advantageously selected from the above group.

The gums include plant saps or tree saps, which solidify when exposed to air, forming resins, or extracts from aqueous plants. Within the meaning of the present invention, for example gum arabic, locust bean gum, gum tragacanth, gum karaya, guar gum, pectine, gellan gum, carrageen, agar, alginate gum, chondrus, xanthan gum may be advantageously selected from this group.

Further, the use of derivatised gums such as, e.g., Hydroxypropyl Guar (Jaguar® HP 8) is advantageous.

The polysaccharides and polysaccharide derivatives include, e.g., hyaluronic acid, chitin and chitosan, chondroitin sulfate, starch and starch derivatives.

The cellulose derivatives include, e.g., methylcellulose, carboxymethylcellulose, hydroxyethylcellulose, hydroxypropylmethylcellulose.

The phyllosilicates include naturally occurring and synthetic alumina such as, e.g., montmorillonite, bentonite, hectorite, laponite, magnesium aluminium silicates such as Veegum®. These may be used as such or in modified form such as, e.g., stearyl alkonium hectorite.

Further, silica gels may also be advantageously used.

The polyacrylates include, e.g., Carbopol types of the company Lubrizol (Carbopol 980, 981, 1382, 5984, 2984, EDT2001 or Pemulen TR2).

The polymers include, e.g., polyacrylamide (Sepigel 305), polyvinyl alcohols, PVP, PVP/VA copolymers, polyglycols.

According to the invention, the preparations present as emulsions contain one or more emulsifiers. These emulsifiers may be advantageously selected from the group consisting of the non-ionic, anionic, cationic or amphoteric emulsifiers.

The non-ionic emulsifiers include
a) Partial fatty acids and fatty acid esters of multivalent alcohols and their ethoxylated derivatives (e.g., glyceryl monostearate, sorbitan stearate, glyceryl stearyl citrate, sucrose stearate)
b) Ethoxylated fatty alcohols and fatty acids
c) ethoxylated fatty amines, fatty acid amides, fatty acid alkanol amides
d) alkylphenol polyglycol ether (e.g., Triton X)

The anionic emulsifiers include
a) soaps (e.g. sodium stearate)
b) fatty alcohol sulfates
c) mono-, di- and trialkyl phosphoric acid esters and their ethoxylates The cationic emulsifiers include
a) quaternary ammonium compounds with a long-chain aliphatic moiety e.g., distearyldimonium chloride The amphoteric emulsifiers include
a) Alkyl aminino alkanoic carboxylic acids
b) Betaines, sulfobetaines
c) Imidazolin derivatives Further, there are naturally occurring emulsifiers, including beeswax, lanolin, lecithin and sterols.

O/W emulsifiers may be advantageously selected, for example, from the group consisting of polyethoxylated or polypropoxylated or polyethoxylated and polypropoxylated products, e.g.:
of fatty alcohol ethoxylates
of ethoxylated lanolin alcohols,
of polyethylene glycol ethers of the general formula
R-O-(—CH2-CH2-O-)$_n$—R',
of fatty acid ethoxylates of the general formula R—COO—(—CH$_2$—CH$_2$—O—)$_n$—H, of etherified fatty acid ethoxylates of the general formula R—COO—(—CH$_2$—CH$_2$—O—)$_n$—R', of esterified fatty acid ethoxylates of the general formula R—COO—(—CH$_2$—CH$_2$—O—)$_n$—C(O)-R\ of polyethylene glycol glycerin fatty acid esters
of ethoxylated sorbitan esters
of cholesterol ethoxylates
of ethoxylated triglycerides
of the alkyl ether carboxylic acids of the general formula R—O—(—CH$_2$—CH$_2$—O—)$_n$—CH$_2$—COOH where n represents a number between 5 and 30,
of polyoxyethylene sorbitan fatty acid esters,
of the alkyl ether sulfates of the general formula R—O—(—CH$_2$—CH$_2$—O—)$_n$—SO$_3$—H
of the fatty alcohol propoxylates of the general formula R—O—(—CH$_2$—CH(CH$_3$)—O—)$_n$—H, of the polypropylene glycol ethers of the general formula R—O—(—CH$_2$—CH(CH$_3$)—O—)$_n$—R', of the propoxylated lanolin alcohols,
of the etherified fatty acid propoxylates R—COO—(—CH$_2$—CH(CH$_3$)—O—)$_n$—R', of the esterified fatty acid propoxylates of the general formula R—COO—(—CH$_2$—CH(CH$_3$)—O—)$_n$—C(O)—R',
of the fatty acid propoxylates of the general formula R—COO—(—CH$_2$—CH(CH$_3$)—O—)$_n$—H, of the polypropylene glycol glycerin fatty acid esters
of the propoxylated sorbitan esters
of the cholesterol propoxylates
of the propoxylated triglycerides
of the alkyl ether carboxylic acids of the general formula R—O—(—CH$_2$—CH(CH$_3$)O—)$_n$—CH$_2$—COOH of the alkyl ether sulfates or the acids on which these sulfates are based of the general formula R—O—(—CH$_2$—CH(CH$_3$)—O—)n-SO$_3$—H of the fatty alcohol ethoxylates/propoxylates of the general formula R—O-Xn-Ym-H, of the polypropylene glycol ethers of the general formula R—O-Xn-Ym-R, of the etherified fatty acid propoxylates of the general formula R—COO-Xn-Y$_m$—R\ of the fatty acid ethoxylates/propoxylates of the general formula

R—COO-Xn-Y$_m$—H.

Particularly advantageous according to the invention are the used polyethoxylated or polypropoxylated or polyethoxylated and polypropoxylated O/W emulsifiers selected from the group consisting of substances with HLB values of 11-18, particularly advantageous with HLB values of 14.5-15.5, provided the O/W emulsifiers have saturated moieties R and R. If the O/W emulsifiers have unsaturated moieties R and/or R, or if isoalkyl derivatives are present, the preferred HLB value of such emulsifiers may be lower or higher.

It is of advantage to select the fatty alcohol ethoxylates from the group consisting of ethoxylated stearyl alcohols, cetyl alcohols, cetyl stearyl alcohols (cetearyl alcohols). Particularly preferred are:

Polyethylene glycol (13) stearyl ether (Steareth-13), Polyethylene glycol (14) stearyl ether (Steareth-14), Polyethylene glycol (15) stearyl ether (Steareth-15), Polyethylene glycol (16) stearyl ether (Steareth-16), Polyethylene glycol (17) stearyl ether (Steareth-17), Polyethylene glycol (18) stearyl ether (Steareth-18), Polyethylene glycol (19) stearyl ether (Steareth-19), Polyethylene glycol (20) stearyl ether (Steareth-20), Polyethylene glycol (12) isostearyl ether (Isosteareth-12), Polyethylene glycol (13) isostearyl ether (Isosteareth-13), Polyethylene glycol (14) isostearyl ether (Isosteareth-14), Polyethylene glycol (15) isostearyl ether (Isosteareth-15), Polyethylene glycol (16) isostearyl ether (Isosteareth-16), Polyethylene glycol (17) isostearyl ether (Isosteareth-17), Polyethylene glycol (18) isostearyl ether (Isosteareth-18), Polyethylene glycol (19) isostearyl ether (Isosteareth-19), Polyethylene glycol-(20) isostearyl ether (Isosteareth-20), Polyethylene glycol (13) cetyl ether (Ceteth-13), Polyethylene glycol (14) cetyl ether (Ceteth-14), Polyethylene glycol (15) cetyl ether (Ceteth-15), Polyethylene glycol (16) cetyl ether (Ceteth-16), Polyethylene glycol (17) cetyl ether (Ceteth-17), Polyethylene glycol (18) cetyl ether (Ceteth-18), Polyethylene glycol (19) cetyl ether (Ceteth-19), Polyethylene glycol (20) cetyl ether (Ceteth-20), Polyethylene glycol (13) isocetyl ether (Isoceteth-13), Polyethylene glycol (14) isocetyl ether (Isoceteth-14), Polyethylene glycol (15) isocetyl ether (Isoceteth-15), Polyethylene glycol (16) isocetyl ether (Isoceteth-16), Polyethylene glycol (17) isocetyl ether (Isoceteth-17), Polyethylene glycol-(18) isocetyl ether (Isoceteth-18), Polyethylene glycol (19) isocetyl ether (Isoceteth-19), Polyethylene glycol (20) isocetyl ether (Isoceteth-20), Polyethylene glycol (12) oleyl ether (Oleth-12), Polyethylene glycol (13) oleyl ether (Oleth-13), Polyethylene glycol (14) oleyl ether (Oleth-14), Polyethylene glycol (15) oleyl ether (Oleth-15), Polyethylene glycol (12)lauryl ether (Laureth-12), Polyethylene glycol (12) isolauryl ether (Isolaureth-12).

Polyethylene glycol (13) cetylstearyl ether (Ceteareth-13), Polyethylene glycol (14) cetyl stearyl ether (Ceteareth-14), Polyethylene glycol (15) cetyl stearyl ether (Ceteareth-15), Polyethylene glycol (16)-cetyl stearyl ether (Ceteareth-16), Polyethylene glycol (17) cetyl stearyl ether (Ceteareth-17), Polyethylene glycol (18) cetyl stearyl ether (Ceteareth-18), Polyethylene glycol (19) cetyl stearyl ether (Ceteareth-19), Polyethylene glycol (20) cetyl stearyl ether (Ceteareth-20), Further it is of advantage to select the fatty acid ethoxylates from the following group:

Polyethylene glycol (20) stearate, Polyethylene glycol (21) stearate, Polyethylene glycol (22) stearate, Polyethylenglycol (23) stearate, Polyethylene glycol (24) stearate, Polyethylene glycol (25) stearate, Polyethylene glycol (12) isostearate, Polyethylene glycol (13) isostearate, Polyethylene glycol (14) isostearate, Polyethylene glycol (15) isostearate, Polyethylene glycol (16) isostearate, Polyethylene glycol-(17) isostearate, Polyethylene glycol (18) isostearate, Polyethylene glycol (19) isostearate, Polyethylene glycol (20) isostearate, Polyethylene glycol (21) isostearate, Polyethylene glycol (22) isostearate, Polyethylene glycol (23) isostearate, Polyethylene glycol (24) isostearate, Polyethylene glycol (25) isostearate, Polyethylene glycol (12) oleate, Polyethylene glycol (13) oleate, Polyethylene glycol (14) oleate, Polyethylene glycol (15) oleate, Polyethylene glycol (16) oleate, Polyethylene glycol (17) oleate, Polyethylene glycol-(18) oleate, Polyethylene glycol (19) oleate, Polyethylene glycol (20) oleate Sodium laureth-11-carboxylate may be advantageously used as ethoxylated alkyl ether carboxylic acid or its salt.

Sodium laureth 1-4 sulfate may be advantageously used as alkyl ether sulfate.

Polyethylene glycol (30) cholesteryl ether may be advantageously used as ethoxylated cholesterol derivative. Also Polyethylene glycol (25) soy sterol has proved to be useful.

Polyethylene glycol (60) Evening Primrose Glycerides may be advantageously used as ethoxylated triglycerides.

Further it is of advantage to select the polyethylene glycol glycerin fatty acid esters from the group consisting of polyethylene glycol (20)glyceryl laurate, polyethylene glycol (21)glyceryl laurate, polyethylene glycol (22)glyceryl laurate, polyethylene glycol (23)glyceryl laurate, polyethylene glycol (6)glyceryl caprate/caprinate, polyethylene glycol (20)glyceryl oleate, polyethylene glycol (20)glyceryl isostearate, polyethylene glycol (18)glyceryl oleate/cocoate.

It is also beneficial to select the sorbitan esters from the group consisting of polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following advantageous W/O emulsifiers may be employed: fatty alcohols having 8 to 30 carbon atoms, monoglycerides of saturated and/or unsaturated, branched and/or non-branched alkanoic carboxylic acids of a chain length of 8 to 24, particularly 12-18 C atoms, diglycerides of saturated and/or unsaturated, branched and/or non-branched alkanoic carboxylic acids of a chain length of 8 to 24, particularly 12-18 C atoms, monoglycerol ethers of saturated and/or unsaturated, branched and/or non-branched alcohols of a chain length of 8 to 24, particularly 12-18 C atoms, diglycerol ethers of saturated and/or unsaturated, branched and/or non-branched alcohols of a chain length of 8 to 24, particularly, 12-18 C atoms, propylene glycol esters of saturated and/or unsaturated, branched and/or non-branched alkanoic carboxylic acids of a chain length of 8 to 24, particularly, 12-18 C atoms and sorbitan esters of saturated and/or unsaturated, branched and/or non-branched alkanoic carboxylic acids of a chain length of 8 to 24, particularly, 12-18 C atoms.

If in the embodiments according to the present invention the emulsion is present in the form of a W/O emulsion, it is advantageous according to the invention to select one or more W/O emulsifiers from the group consisting of the compounds of polyglyceryl isostearate, ethoxylated stearates, ethoxylated hydrated castor oils, alkyl isostearates, ethoxylated dodeceyl glycol copolymers and lanolin derivatives.

Here, the use of the W/O emulsifiers polyglyceryl-3diiosostearate and PEG-30 dipo-lyhydroxystearate is preferred according to the invention.

If in the embodiments according to the present invention the emulsion is present in form of a W/O emulsion, it is advantageous according to the invention to select one or more W/O emulsifiers from the group consisting of the compounds of ethoxylated-proxylated alkyl modified dimethicone and dimethicone copolyol.

Here, the use of W/O emulsifiers Dimethiconcopolyol and Cetyl PEG/PPG-10/1 Dimethicone is preferred according to the invention.

In addition, it has surprisingly shown that the fragrance impression of a cosmetic preparation is noticeably increased by adding 4-hydroxyacetophenone in comparison with a preparation that does not contain any 4-hydroxyacetophenone.

This is the more surprising as, particularly, 4-hydroxyacetophenone and its analogues and, particularly, 4-hydroxyacetophenone-containing skin care products may produce a side smell that is perceived by the user as unpleasant.

Especially when 4-hydroxyacetophenone was formulated as a component of a body lotion and the initial volatile perfume components evaporated, a side smell may develop which is to be attributed to 4-hydroxyacetophenone.

Therefore, also substance combinations of 4-hydroxyacetophenone and one or more perfume substances are considered an advantageous embodiment of the present invention.

The following advantageous perfume substances may be employed: dipropylene glycol, methyl dihydrojasmonate, phenethyl alcohol, linalool, linalyl acetate, 2,6-Dimethyl-7-octen-2-ol, alpha hexylcinnamaldehyde, 2-Acetonapthone-1,2,3,4,5,6,7,8-octahydro-2,3,8,8-tetramethyl, p-t-Butyl-alpha-methyldihydrocinnamicaldehyde, Benzyl acetate, 1,3,4,6,7,8-Hexahydro-4,6,6,7,8,8-hexamethylcyclopenta-gamma-2-benzopyran, Methyl cedryl ketone, Ethylene brassylate, 4-(4-Hydroxy-4-methylpentyl)-3-cyclohexene-1-carboxyaldehyde, Benzyl salicylate, Hexyl salicylate, Orange oil, alpha-Isomethylionone, Diethyl phthalate, 4-t-Butylcyclohexyl acetate, Patchouli oil, 3,7-Dimethyl-2,6-octadien-1-ol, Tetrahydroiinaiooi, Hydroxycitronellal, Isopropyl myristate, 3,7-Dimethyl-6-octen-1-ol, Orange terpenes, Heliotropin, Terpinyl acetate, omega-Pentadecalactone, Methyl-alpha-ionone, Lavandin oil, Lemon oil, Bergamot oil, 7-Acetyl-1,1,3,4,4,6-hexamethyltetralin, Coumarin, Ethyllinalool, Amyl salicylate, 2-tert-Pentyl-cyclohexyl acetate, 3-Methyl-5-phenyl-1-pentanol, Cedrol, Benzyl benzoate, Vanillin, alpha-Amylcin-namaldehyde, Dimethyl phthalate, d-Limonene, 2-Isobutyl-4-hydroxy-4-methyltetrahydropy-ran, Triethyl citrate, Terpineol, Lavender oil, Diethylene glycol monoethyl ether, 2-Phen-oxyethyl isobutyrate, Anisyl alcohol, 3-Pentyltetrahydro(2H)pyranyl acetate, Methyl ester of rosin, partially hydrogenated, Isobornyl acetate, Rosemary oil, Petitgrain oil, 1,4-Dioxa-cyclo-hexadecane-5,16-dione, Isoamyl salicylate, gamma-Undecalactone, alpha-lonone, Oxacyclo-hexadecen-2-one, 7-Octen-2-ol, 2-methyl-6-methylene, dihydro derive, 1,2-Propyleneglycol, 3-(5,5,6-Trimethylbicyclo(2.2.1)hept-2-yl) cyclohexan-1-ol, Geranium oil, Musk ketone, Cedre-nyl acetate, Isobornylcyclohexanol, Ionone, Benzyl alcohol, gamma-Nonalactone, I-Menthol, Cyclohexyl salicylate, Dihydromyrcenyl acetate, Citral, Orange terpenes (natural), Cedar-wood oil, alpha-Pinene, Majantol, Phenoxyethanol, Ethyl acetate, Cedrol methyl ether, 1,5,9-Trimethyl-13-oxabicyclo(10.1.0) trideca-4,8-diene, Peppermint oil, Eugenol, Ethyl maltol, Benzaldehyde, Cinnamic alcohol, 3,7-Dimethyl-1-octanol, alpha-Methyl-3,4-methylene dio-xyhydrocinnamic aldehyde, beta-Pinene, d-Camphor, Methyl abietate, Cedryl acetate, Ylang ylang oil, Sandalwood oil, Mineral oil, Dimethyl benzyl carbinyl butyrate, Ethyl butyrate, Ge-ranyl acetate, Hexylene glycol, Myrcene, alpha-Methyionantheme, beta-lonone, 3-(4-t-Butylphenyl) propanal, 3,7-Dimethyloctan-3-yl acetate, Acetic acid, (1-oxopropoxy)-1-(3,3-dimethylcyclohexyl), Eucalyptol, 4-Carvomenthenol, Stearic acid, Menthanyl acetate, *Eucalyptus* oil, Dihydroterpinyl acetate, o-t-Butylcyclohexyl acetate, Isoeugenol, alpha-Terpineol, Cyclamen aldehyde, Hydroxycitronellol, Myrcenyl acetate, Nopyl acetate, 3,7-Dimethyl-1,3,6-octatriene, Rhodinol, Dimethyl benzyl carbinyl acetate, Tricyclodecenyl Propionate, 2-Methyl-5-phenylpentan-1-ol, Sclareoate, 3-Isocamphyl cyclohexanol, trans-Anethole, Hexahydro-4,7-methanoinden-5(6)-yl acetate, 4-(p-Hydroxyphenyl)-2-butanone, Nerolidol, alpha- Butylcinnamaldehyde, Bornyl acetate, Etyhl methylphenylglycidate, trans-beta-Ionone, Camphene, Juniper berry oil, Mandarin oil, Nutmeg oil, Spearmint oil, Grapefruit oil, Lab-danum oil, *Galbanum* oil, Menthone, Trichloromethyl phenyl carbinyl acetate, alpha-Methyl-benzyl acetate, Ethyl-2methyl-1,3-dioxolane-2-acetate, 2,6-Nonadienal, Abietyl acetate, A-nisic acid, Diphenyl ether, Triacetin, 2-Methyl-4-phenyl-2-butanol, Phenylethyl acetate, 1-Phenyl-3-methyl-3-pentanol, Anisyl acetate, Cinnamic aldehyde, p-Methylanisole, 5-Phenyl-pentanol, Diethyl malonate, Citronellal, Nerol, Undecanal, 2-methyl-, Hexyl alcohol, Glyceryl caprylate, Methyl 2-nonenoate, Octyl acetate, Decanal, Lauryl alcohol, Lauric aldehyde, Ethyl vanilline, 3-Phenyl-1-propanol, Octanal, Butylated hydroxytoluene, 4-Acetyl-6-t-butyl-1,1-di-metylindane, delta-3-Caren, Benzyl laurate, Neryl acetate, Ethyl acetoacetate, Hexyl acetate, Menthol liquid, Citronellyl acetate, Tetrahydromyrcenol, Diacetin, Menthyl acetate, 3(4),8(9)-Dihydroxymethyl tricyclo (5.2.1.0(2,6)decane, 2,4-Dimethyl-3-cyclohexen-1-carboxaaldehyde, Cedrenol, Phenylacetaldehyde glyceryl acetal, Sabinene, 3,7,11-Trimethyl-1,2,10,-dode-catrien-3-ol (eis & trans), Octyldodecanol, Formaldehyde cyclododecyl ethyl acetal, Myristi-cin, 3,7-Dimethyl-2(3),6-nonadienenitrile, Ethyllinylyl acetate, 2-Methylbutyl acetate, cis-3-Hexenyl salicylate, 2-Methyl-4-(2,6,6-trimethyl-2(1)-cyclohexen-1-yl) butanal, Maltol isobuty-rate, 2-Methyl-3(4-(2-methyl-propyl)phenyl)propanal, 12-Oxahexadecanolide, 1,1-Dimethoxy-2,25-trimethyl-4-hexene, 1,6,7,8-Tetrahydro-1,4,6,6, 8,8-hexamthyl-as-indacen-3<2H>-one, Bergamot oil, bergaptene free, Treemoss abs., Citrus oil distilled, Lemon terpenes, gamma-Decalactone, 2-Methyl-4-phenyl-2-pentanone, Allyl phenoxyacetate, Methyl-delta-ionone, Ci-tronella oil, Clove bud oil, Thyme oil, Lime oil, Bois de rose oil, Cognac oil, Neroli bigarade oil, Spike lavender oil, Vetiver oil, Fir needle oil, Methylpentenolone, Lemon oil terpenes, Isobutyl salicylate, beta-Caryophyllene, Pulegone, Thymol, gamma-Terpinene, Acetyl Hexa-methyl Tetralin (musk compounds), amyl acetate, amyl salicylate, anethol, anise oil, annatto, extract from the leaves of melissa, oil from the leaves of melissa, bay leaf oil, laurel oil, benzaldehyde, benzyl acetate, benzyl alcohol, benzyl benzoate, benzyl cinnamate (ingredient of etheric oils), benzyl salicylate, benzyl cinnamate, calendula oil, *camellia* oil, camphor, caraway oil, cardamom oil, carvone, chamomile oil, cinnamon oil, citral, lemon grass oil, clove oil, clove leave oil, coumarine, cumin extract, cimethyl brassylate, dipentene, ethyl vanilline, ethylene brassylate, eucalyptol, *eucalyptus* oil, eugenol, ginger oil, Gum Benzoin, hop oil, isoamyl acetate, juniper tar, lavender oil, lemon oil, lemon grass oil, lovage oil, chamomile oil, menthol, menthyl acetate, menthyl lactate, menthyl salicylate, methyl eugenol, methyl rosinate, methyl dihydrojasmonate, nutmeg oil, Ocotea Cymbarum oil, frankincence, frankincence extract, orange extract, orange blossom oil, orange blossom water, orange peel extract, parsley oil, p-Cymene, pentadecalactone, peppermint extract, peppermint oil, phenethyl alcohol, pine oil, pine(tar) oil, rose extract, rose oil, rosemary oil, rue oil, sage oil, elder extract, elder oil, sandalwood oil, *sassafras* oil, (sweet) marjoram oil, creosote, tea tree oil, terpineol, thyme oil, thymol, vanilla, vanilline, yarrow oil.

The following raw materials may be used as further stabilizers:

Acetyl trifluoromethylphenyl valylglycine, acrylamide ammonium acrylate copolymer, aluminium-magnesium hydroxide stearate, ammonium lactate, ammonium polyacrylate, ammonium polyacryloyldimethyl taurate, Arginin PCA, caprylyl salicyl acid ester, cinnamic acid, cocoglucoside, copper-gluconate, diphenyl dimethicone, disodium adenosine triphosphate, disodium succinate, disteardimonium hectorite, dodecene, Eperua Falcata, hydrated palm glyceride, hydrated palm glyceride citrate, hydrated palm kernel glycerides, hydrolysed wheat protein PG-propylmethylsilanediol, hydroxyethyl acrylate/sodiumacryloyl dimethyl taurate copolymer, Isodeceth-6, Linseed Acid, magnesium aspartate, melibiose, Oxothiazolidine carboxylic acid, Palmitoyl pentapeptide 4, PEG-8 Laurate, phenethyl alcohol, phenyl propanol, polyacrylate-13, polyacrylate-3, Sarcosin, Saxifraga *Sarmentosa* Extract, Scutellaria *Baicalensis* Extract, sodium metabisulfite, soy isoflavone, tocopheryl glucoside, Trideceth-6, zinc gluconate, Triacetin, 1,2 Hexandiol, Hydroxyethylpiperazine Ethane Sulfonic Acid, Nicotinamide, Penethyl Alcohol, Penthylene Glycol, Camauba Wax, Chlorhexidine Digluconate, Oleyl Erucate, Polycaprolactone, Su-crose Polycottonseedate, Acetyl Trifluoromethylphenyl Valylglycin, Phytol, *Avena* Aqua, Nylon-66, Hydroxyethylpiperazine Ethane Sulfonic Acid, Hydroxypropyl Tetrahydropyrantriol, Shorea Robusta Butter, Punica Granatum Fruit Juice, Methylserin, Ascorbyl Tocopheryl Ma-leate, Poly C10-30 Alkyl Acrylate, Pyracantha Fortuneana Extract, PEG-24 Cetyl Ether, Thiodipropionic Acid, Essential Oils, Tocopheryl Glucoside, PEG-24 Cholesteryl Ether, Biosaccharide Gum 3, Guanosine, Polyester-5, Dimethoxy Di-p-Cresol, Tri C14-15 Alkylcitrate, Ethyl Bisiminomethylguaiacol Manganese Chloride, Hydrated Magnesium Silicate, *Lagerstroemia Indica* Extract, Ethyl Glucoside, Linseed Acid, PEG/PPG-14/7 Dimethyl Ether, Sodium Dodecylbenzene Sulfonate, Isoquercitrin, Thiotaurine, Andrographolide, Erythritol, Xymeny-nic Acid, *Coffea Robusta*, Disodium NADH, Lauryl Dimonium Hydroxypropyl Hydrolyzed Soy Protein, Methylsilanol/Silicate Crosspolymer, *Amaranthus Caudatus* Extract, BGT, Chrysanthenum *Parthenium*, Lauryl Polyglucoside, Sodium Hydroxypropyl Starch Phosphate, PEG-60 Glyceryl Isostearate, Glucosylrutin, Mineral Water, Pisces Collagen, Sodium Hydroxyethyl Acrylate/Acryloyldimethyl Taurate Copolymer, Sodium Mannose Phosphate, Tetrahydrobis-demethoxycurcumin, Tetrahydro-demethoxycurcumin, Tetrahydro-demethoxydiferuloyl methane, Butylhydrochinone, Citrus Aurantium *Dulcis* Blossoms, Hierochloe *Odorata* extract, Kaempferia Galanga Root Extract, PEG-2 Stearyl Ether, Succinoglycan, Trioctyldodecyl Citrate, Coleus *Barbatus* Extract, Eclipta *Prostrata* Extract, PEG-10 Dimethicone/Vinyl Dimethicone Crosspolymer, Polyglyceryl-2 Caprate, *Pyrus* Malus Water, Trioxaundecanedioic Acid, *Amaranthus* Extract, Dodecene, Hydrolyzed Cera Alba, Oxothiazolidinecarboxylic Acid, PEG-20 Stearyl Ether, *Platanus Occidentalis*, Selaginella Tamariscina Extract, Tetrahydrobisdeme-thoxydiferuloylmethane, *Anthemis Nobilis* Flower, *Cassia Alata*, Echium Lycopsis Oil, Eucalyptol, Heptapeptide-6, *Humulus Japonicus* Flower/Leaf/Stem Extract, Hydrogenated Myristyl Olive Esters, Hydrolyzed Wheat Protein PG-Propyl Methylsilanediol, *Lupinus Luteus* Extract, Palmitoyl Lysyl Aminovaleroyl Lysine, Palmitoyl Tetrapeptide-10, Polyglyceryl-6 Polyricinoleate.

Preferred within the meaning of the present invention are pigment mixtures of white pigments (e.g. kaolin, titanium dioxide or zinc oxide) and inorganic colour pigments (e.g., iron oxide pigments, chromium oxides), wherein the pigments may be present in coated or uncoated form. Among the colour pigments the iron oxides are particularly preferred. The pigments according to the invention may be inorganic or organic.

White pigments are pigments the optical effect of which is mainly based on non-selective light scattering (cf. also DIN 55944: 2003-11). Inorganic white pigments may be distinguished from the chemically often very similar filling materials mainly by their generally higher refractive index and—in context with this—their higher scattering ability as well by their use according to DIN 55943: 2001-10.

White pigments preferably used according to the invention do not show any absorption in the range of visible light, but a high scattering ability instead, which has as a consequence a high covering ability. The scattering ability is the higher the larger the difference is between the refractive index of the white pigment and of the surrounding medium.

White pigments that are advantageous according to the invention are titanium dioxides (refractive indices: 2.55 for Anatas and 2.75 for Rutil) and zinc oxides (refractive index between 1.95 and 2.1). Titanium dioxide is particularly preferred.

Advantageous within the meaning of the present invention may also be pigment(s) selected from the group consisting of effect pigments, which confer to the cosmetic preparation an additional property besides the pure colour—such as, for example, an angular dependence of the colour (changing, flopping), lustre (not surface lustre) or texture. These effect pigments are advantageously used according to the invention in addition to one or more white and/or colour pigments.

The major group of effect pigments is represented by the lustre pigments, including, according to DIN 55944: 2003-11 metal effect pigments and pearlizing pigments. A number of particular effect pigments cannot be allocated to these two groups, e.g., platelet-shaped graphite, platelet-shaped iron oxide and micronized titanium dioxide, wherein micronized titanium dioxide does not create a lustre effect, but an angular-dependent light scattering effect. The lustre pigments of DIN 55943: 2001-10 are mainly platelet-shaped effect pigments. When in parallel orientation, lustre pigments exhibit a characteristic lustre. The optical effect of lustre pigments is based on the directed reflection at metal particles (metal effect pigments), at transparent particles with a high refractive index (pearlizing pigments) or the phenomenon of interference (interference pigments) (DIN 55944: 2003-11).

Examples of preferred customary effect pigments according to the invention are: Timiron® by Merck, Iriodin® by Merck (pearlizing and colour lustre pigments for decorative technical applications), Xirallic® by Merck (colour-intensive crystal effect pigments).

Further, the preparations according to the invention may advantageously also contain organic colour pigments, i.e., organic colours which are practically insoluble in the preparation. According to DIN 55944: 1990-04, organic pigments can be classified into azo pigments and polycyclical pigments from a chemical perspective and into coloured or black pigments according to colour aspects. Organic white pigments are of no practical significance.

The pigments may be advantageously applied, within the meaning of the present invention, also in form of commercially available oily or aqueous preliminary dispersions.

It is further advantageous within the meaning of the present invention, if the preparation according to the invention comprises one or more colouring agents.

The colouring agents can be both of synthetic and of natural original.

The colouring agents suitable and approved for cosmetic purposes may be used. Examples are cochenille red A (C.I. 16255), patent blue V (C.1.42051), indigotine (C.1.73015), chlorophylline (C.1.75810), quinoline yellow (C.I.47005), titanium dioxide (C.1.77891), indanthrene blue RS (C.I. 69800) and madder lake (C.I.58000).

These colouring agents are usually formulated in concentrations of 0.001 to 1% by weight, based on the total mixture.

The preparations of the invention may also contain repellents.

Most repellant agents include the substance classes of amides, alcohols, esters and ethers.

A modern repellent agent is, for example, 1-Piperidine carboxylic acid 2-(2-hydroxy-ethyl)-1-methyl propyl ester (INN: Icaridin, CAS Number: 119515-38-7, EINECS number: 423-210-8), having the following structure:

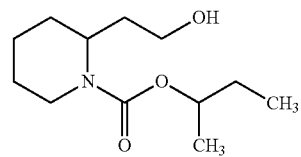 [SMILES: CCC(C)OC(=O)N1CCCCC1CCO]

Another frequently used repellent agent is 3-(N-n-Butyl-N-acetyl-amino)-propionic acid ethyl ester (also referred to as Ethylbutylacetylaminopropionate or repellent 3535), which is characterized by the following structural formula:

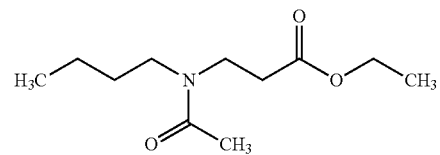

Not lastly, the skilled person knows the repellent agent N,N-Diethyl-3-methylbenzamide (commercial name: Metadelphene, DEET), having the following structure:

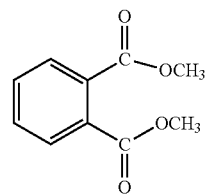 [SMILES: COC(=O)c1ccccc1C(=O)OC]

Actives can also be added to the formulations according to the invention.

The actives include, for example, tocopherol, tocopherol acetate, tocopherol palmitate, ascorbic acid, (Desoxy)Ribonucleic acid and their fragmentation products, β-glucans, retinol, bisabolol, allantoin, phytantriol, panthenol, AHA acids, amino acids, ceramides, pseudo ceramides, essential oils, plant extracts such as, e.g., *prunus* extract, bamboo extract, linden flower extract and vitamin complexes.

A particular embodiment of the invention, comprising the preparations according to the invention, comprises at least a compound, selected from vitamins, allantoin, bisabolol, glyceryl glucoside and plant extracts.

In a preferred embodiment of the invention, comprising the preparations according to the invention, at least one compound selected from tocopherol, tocopherol acetate, tocopherol palmitate, ascorbic acid, urea, β-glucans, retinol, bisabolol, allantoin, phytantriol, panthenol, AHA acids, plant extracts and mixtures thereof.

The following examples are intended to explain the invention, but not to restrict it.

| Exemplary Formulation 1 | % by weight |
|---|---|
| Stearic acid | 2 |
| Glyceryl stearate | 2 |
| Cetyl alcohol | 2 |
| Isohexadecane | 2 |
| Dicaprylyl ether | 4 |
| C12-15 alkyl benzoate | 4 |
| Myristyl myristate | 1 |
| Sunflower oil | 1 |
| Liquorice extract | 0.1 |
| Carrageenan | 0.2 |
| Carbomer | 0.3 |
| Methylparaben | 0.4 |
| 4-hydroxyacetophenone | 0.7 |
| Glycerol | 5 |
| EDTA | 0.2 |
| Perfume | 0.2 |
| Sodium hydroxide (set to pH 7.5) | q.s. |
| Water | ad 100 |

| Exemplary Formulation 2 | % by weight |
|---|---|
| Cetyl stearyl alcohol | 3 |
| Capric/caprylic triglyceride | 3 |
| Dicaprylyl carbonate | 3 |
| Dicaprylyl ether | 2 |
| Octocrylene | 5 |
| Butyl methoxydibenzoylmethane | 1 |
| Sodium stearoyl glutamate | 0.3 |
| 4-hydroxyacetophenone | 0.4 |
| Acrylate/C10-30 Alkyl Acrylate Crosspolymer | 0.4 |
| Xanthan Gum | 0.2 |
| Evening Primrose Seed Oil | 1 |
| Vitamin A palmitate | 0.1 |
| Glycerol | 6 |
| Phenoxyethanol | 0.5 |
| Sodium hydroxide (set to pH 6) | q.s. |
| Water 100% | ad 100 |

| Exemplary Formulation 3 | % by weight |
|---|---|
| Cetyl stearyl alcohol | 3 |
| Caprylic/capric triglyceride | 3 |
| Dicaprylyl carbonate | 3 |
| Dicaprylyl ether | 2 |
| Ethylhexyl methoxycinnamate | 4 |
| Butyl methoxydibenzoylmethane | 1 |
| Sodium stearoyl glutamate | 0.3 |
| 4-hydroxyacetophenone | 0.5 |
| Acrylat/C10-30 Alkyl Acrylat Crosspolymer | 0.4 |
| Xanthan Gum | 0.2 |
| Organic dye, water-soluble | 0.1 |
| Niacin amide | 0.2 |
| Glycerol | 5 |
| Ethylparaben | 0.1 |
| Phenoxyethanol | 0.5 |
| Perfume | 0.3 |
| Sodium hydroxide (set to pH 6) | q.s. |
| Water 100% | ad 100 |

Face Cream

| Exemplary Formulation 4 | % by weight |
|---|---|
| Glyceryl stearate | 2 |
| Stearyl alcohol | 2 |
| Caprylic/capric triglyceride | 3 |
| Dicaprylyl ether | 3 |
| C12-15 Alkyl benzoate | 3 |
| Potassium Cetyl phosphate | 0.3 |
| Camellia sinensis extract (green tea) | 0.1 |
| Tris-Biphenyl Triazine | 1 |
| Diethylhexyl butamido triazone | 1 |
| Ethylhexyl triazone | 1 |
| Terephthaliden Dicamphor sulfonic acid (sodium salt) | 0.5 |
| Ammonium Acryloyldimethyl taurateA/P Copolymer (Aristoflex AVC ®) | 0.4 |
| Xanthan Gum | 0.1 |
| 4-Hydroxyacetophenone | 0.3 |
| Grapeseed oil | 0.5 |
| Rucinol | 0.1 |
| Glycerol | 7 |
| EDTA | 0.2 |
| Preservative | q.s. |
| Sodium hydroxide (set to pH 7.0) | q.s. |
| Water 100% | ad 100 |

| Exemplary Formulation 5 | % by weight |
|---|---|
| Glyceryl stearate | 2 |
| Stearyl alcohol | 1 |
| Caprylic/capric triglyceride | 2 |
| Dicaprylyl carbonate | 3 |
| Dicaprylyl ether | 4 |
| Sodium Stearoyl glutamate | 0.3 |
| Organic colouring agent, oil-soluble, blue | 0.05 |
| 4-Hydroxyacetophenon | 0.3 |
| Acrylate/C10-30 Alkyl Acrylate Crosspolymer | 0.3 |
| Xanthan Gum | 0.2 |
| Ascorbic acid | 0.1 |
| Glycerol | 6 |
| Methylparaben | 0.2 |
| Phenoxyethanol | 0.5 |
| Perfume | 0.4 |
| Sodium hydroxide (set to pH 6) | q.s. |
| Water 100% | ad 100 |

The invention claimed is:

1. A skin care preparation comprising an oil-in-water emulsion, said emulsion comprising:
    (a) 0.3-0.7 % by weight of 4-hydroxyacetophenone,
    (b) at least one anionic emulsifier selected from the group consisting of acyl glutamates, acyl peptides, sarcosinates, taurates, acyl lactylates, alanates, carboxylic acids, ester carboxylic acids, ether carboxylic acids, acyl isethionates, alkyl aryl sulfonates, alkyl sulfonates, sulfosuccinates, alkyl ether sulfates, alkyl sulfates, alkyl ether phosphates, and mixtures thereof, and
    less than about 0.5% by weight of complexing agents or chelators,
    all amounts calculated on the total preparation, wherein said composition has a greater phase stability over time than the same composition without 4-hydroxyacetophenone.

2. The emulsion of claim 1, additionally comprising an electrolyte.

3. The emulsion of claim 2, wherein the electrolyte is sodium hydroxide.

* * * * *